(12) United States Patent
Wigginton et al.

(10) Patent No.: US 11,571,226 B1
(45) Date of Patent: Feb. 7, 2023

(54) BONE CUTTING GUIDE

(71) Applicant: New Standard Device, LLC, San Antonio, TX (US)

(72) Inventors: Robert E. Wigginton, McKinney, TX (US); Shital Perna, Springboro, OH (US); Adam P. Shonebarger, San Antonio, TX (US); Anish D. Vaghela, Boerne, TX (US)

(73) Assignee: New Standard Device, LLC, San Antonio, TX (US)

( * ) Notice: Subject to any disclaimer, the term of this patent is extended or adjusted under 35 U.S.C. 154(b) by 0 days.

(21) Appl. No.: 17/944,378

(22) Filed: Sep. 14, 2022

(51) Int. Cl.
*A61B 17/17* (2006.01)
*A61B 17/15* (2006.01)

(52) U.S. Cl.
CPC ........ *A61B 17/1775* (2016.11); *A61B 17/151* (2013.01); *A61B 17/157* (2013.01); *A61B 17/1764* (2013.01)

(58) Field of Classification Search
CPC combination set(s) only.
See application file for complete search history.

(56) References Cited

U.S. PATENT DOCUMENTS

| | | | |
|---|---|---|---|
| 6,391,031 B1 | 5/2002 | Toomey | |
| 7,972,338 B2 | 7/2011 | O'Brien | |
| 8,114,083 B2 | 2/2012 | Haines | |
| 8,282,645 B2 | 10/2012 | Lawrence et al. | |
| 8,475,463 B2 | 7/2013 | Lian | |
| 10,226,292 B2 | 3/2019 | Lundquist et al. | |
| 10,292,713 B2 * | 5/2019 | Fallin | A61B 17/151 |
| 10,561,426 B1 | 2/2020 | Dayton et al. | |
| 2006/0264961 A1 | 11/2006 | Murray-Brown | |
| 2007/0265634 A1 | 11/2007 | Weinstein | |
| 2014/0257509 A1 | 9/2014 | Dacosta et al. | |
| 2014/0324053 A1 | 10/2014 | Stemniski et al. | |
| 2016/0235414 A1 | 8/2016 | Hatch et al. | |
| 2017/0014143 A1 | 1/2017 | Dayton et al. | |
| 2019/0328436 A1 | 10/2019 | Bays et al. | |
| 2019/0357919 A1 | 11/2019 | Fallin et al. | |

* cited by examiner

*Primary Examiner* — Sameh R Boles
(74) *Attorney, Agent, or Firm* — Gregory K. Goshorn; Greg Goshorn, P.C.

(57) ABSTRACT

Provided is a Bone Cutting Guide (BCG) for facilitating the cutting of a patent's bones that may include an outer shell, comprising an upper shell; and a lower shell; a left guidance sphere, comprising a first plurality of pin guidance holes; and a first guide surface; a right guidance sphere, comprising a second plurality of pin guidance holes; and a second guide surface, wherein the left and right guidance spheres are positioned between the upper and lower shells; and a plurality of fasteners configured to hold the upper and lower shells together and, when tightened, secure the left guidance sphere and right guidance sphere into selected positions.

9 Claims, 7 Drawing Sheets

BONE CUTTING GUIDE

FIELD OF THE DISCLOSURE

The claimed subject matter relates generally to a bone cutting guide and, more specifically, to a device that enables a surgeon to accurately and consistently cut a bone during surgery to correct a bone deformity or to repair the result of trauma to the bone by guiding the angle of cuts

BACKGROUND

With current technology, during surgery to either correct a bone deformity or repair a bone in the event of trauma, surgeon and residents must cut bone without any guide, or "free hand." Typically, two portions of a bone must be cut and then grafted together. In one scenario, the two cuts should ideally be as close to parallel as possible so that two portions that remain fit together accurately. In a different scenario, two bones may need to be cut to a specific relative angle to each other to correct a particular deformity. Free hand cuts may often not be the exact specific angles that are required. Once a bone has been cut in such situations, there are few remedies in the event the cut has been incorrectly or inaccurately executed.

SUMMARY

Provided is a device that provides a cutting guide to enable surgeons and residents to accurately and consistently cut bones during surgery. A bone cutting guide (BCG) for facilitating the cutting of a patent's bones may include an outer shell, comprising an upper shell, a lower shell and pin guidance holes; a left guidance sphere, comprising a first plurality of wire guidance holes and a first guide surface; a right guidance sphere, comprising a second plurality of wire guidance holes and a second guide surface, wherein the left and right guidance spheres are positioned between the upper and lower shells; and a plurality of fasteners configured to hold the upper and lower shells together and, when tightened, secure the left guidance sphere and right guidance sphere into selected positions.

This summary is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed description.

BRIEF DESCRIPTION OF THE DRAWINGS

A better understanding of the claimed subject matter can be obtained when the following detailed description of the disclosed embodiments is considered in conjunction with the following figures, in which:

DETAILED DESCRIPTION OF THE FIGURES

Those with skill in the relevant arts will recognize that the disclosed embodiments have relevance to a wide variety of surgical environments in addition to those described below.

Figure 1:
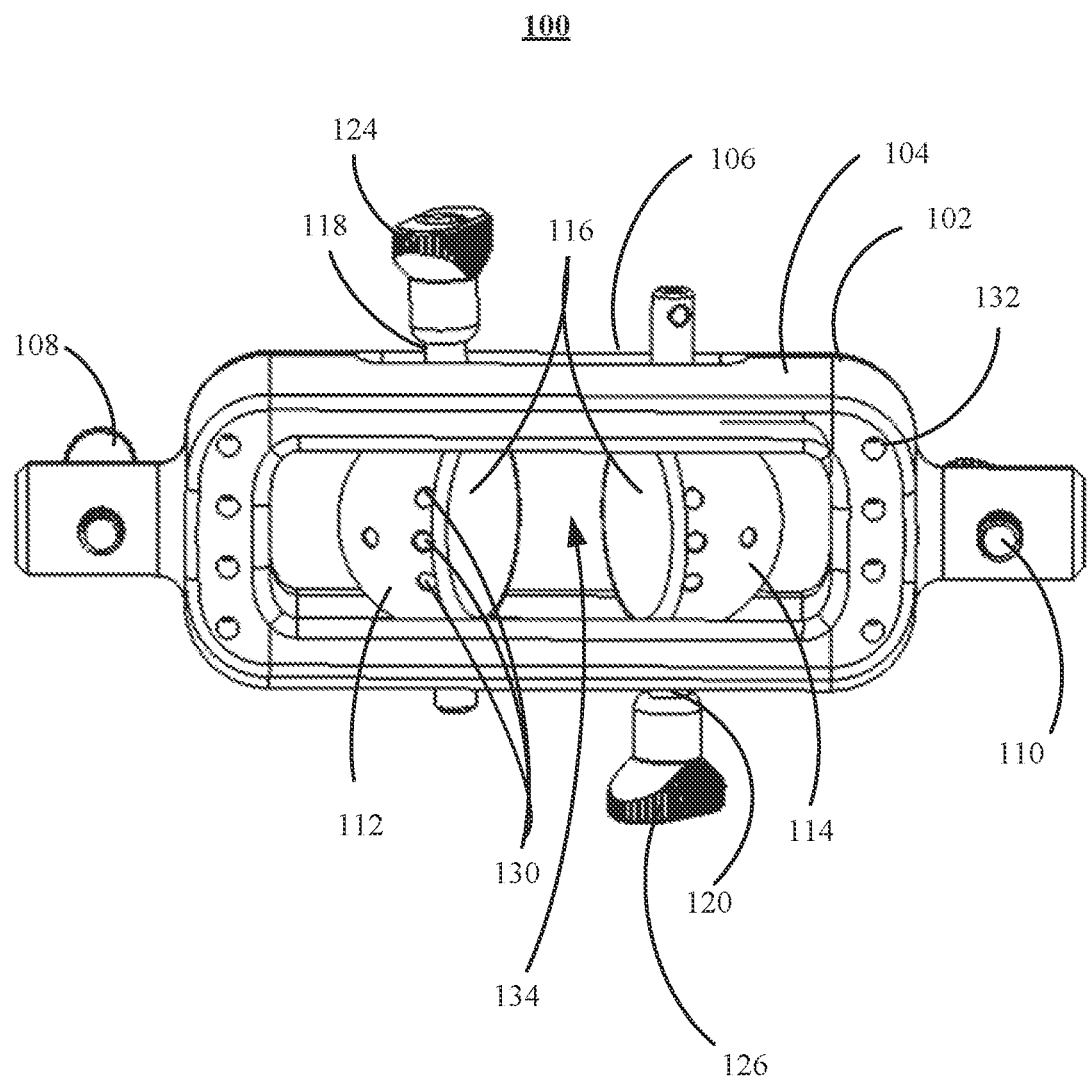
FIG. 1 is an illustration of one embodiment of a disclosed bone cutting guide.

FIG. 1 is an illustration of one embodiment of a Bone Cutting Guide (BCG) 100. BCG 100 has an outer shell 102 that is comprised of an upper shell 104 and a lower shell 106, which can be seen more clearly in FIG. 2. Fasteners, which in this example are wing bolts, 108 and 110 pass through upper and lower shells 104 and 106 and are adapted to press upper and lower shells 104 and 106 together. It should be understood that there are multiple methods able to hold upper and lower shells 104 and 106 together including, but not limited to, bolts and nuts and posts with toggle clamps.

Enclosed within outer shell 102 and in between upper and lower shells 104 and 106 are a pair of guide spheres, i.e., a left guide sphere 112 and a right guide sphere 114. Each of guide spheres 112 and 114 include a guide surface 116 which face each other. Guide surfaces 116 enable a surgeon to align a bone saw or knife to cut a bone at two places such that the resultant cuts are at a selected angle with respect to each other. Left guide sphere 112 is coupled to a threaded guide post 118 and right guide sphere 114 is coupled to a threaded guide post 120. Dome wing nuts with a dome-shaped surface 124 and 126 screw onto guide posts 118 and 120, respectively, and may be tightened to secure left and right guide spheres 112 and 114 into a desired angle with respect to each other. Each of posts 118 and 120 extend from opposing sides of their respective guide spheres 112 and 114, through a guide channel 136 (see FIG. 2) and may be threaded on one or both sides. The dome-shaped surfaces on dome wing nuts 124 and 126 are configured to enable dome wing nuts 124 and 126 to be tightened against outer shell 102 at a variety of angles. It should be understood that are multiple ways to tighten guide spheres 112 and 114 into position including, but not limited to, bolts threaded into spheres 112 and 114 and conventional nuts with a dome-shaped surface rather than posts 118 and 120 with dome wing nuts 124 and 126.

Each of guide spheres 112 and 114 includes a plurality of wire guidance holes 130, which for the sake of simplicity are only labeled on left guide sphere 112. Pin guidance holes 132, which for the sake of simplicity only one or which is labeled, are also included in outer shell 102. Each of pin guidance holes 132 pass through upper shell 104 and lower shell 106. It should be understood that wires may be employed through pin guidance holes 132 rather than pins and pins rather than wires may be employed through wire guidance holes 130. A cutting channel 134 that passes through upper and lower shells 104 and 106 provides space for a surgeon to employ a knife or saw (not shown) to make cuts in a patient's bone or bones and is explained in more detail below in conjunction with FIGS. 5-7.

Figure 2:
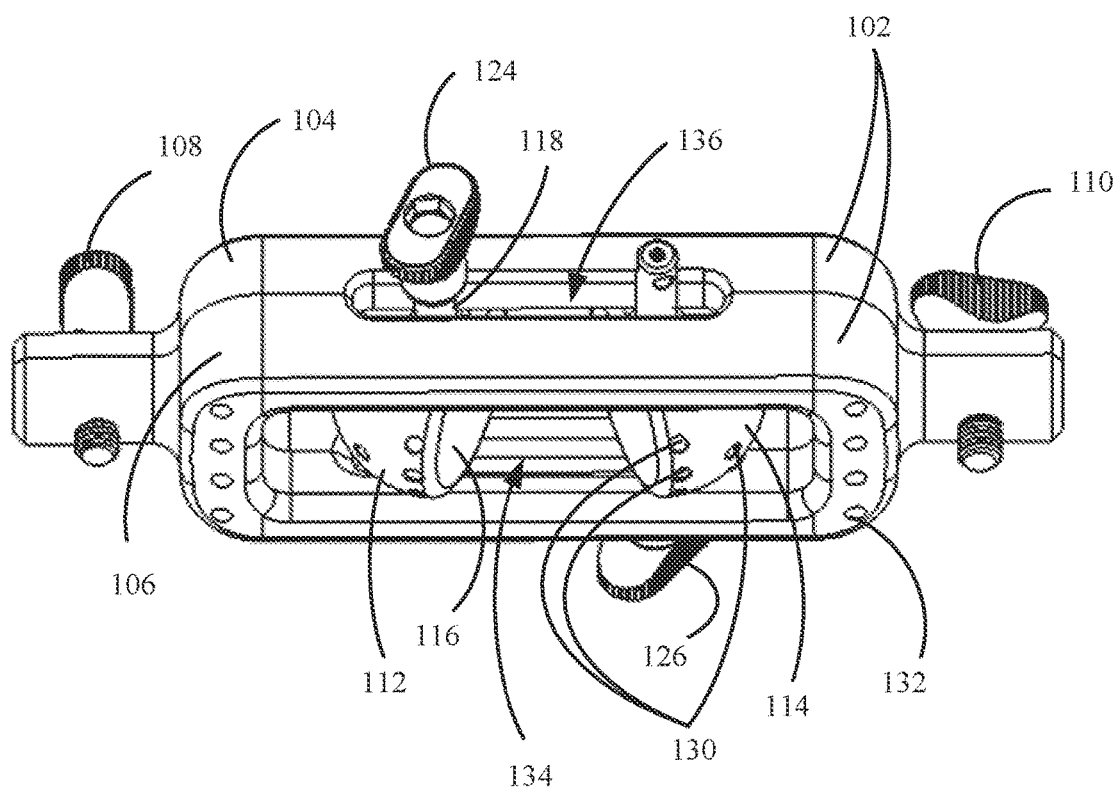
FIG. 2 is an illustration of the bone cutting guide of FIG. 1 from a different perspective showing additional detail.

FIG. 2 is an illustration of BCG 100 of FIG. 1 from a different perspective showing additional detail. Visible in FIG. 2 and introduced above in FIG. 1, are outer shell 102, wing bolts 108 and 110, guide spheres 112 and 114, guide post 118, dome wing nut 124, wire guidance holes 130 and pin guidance holes 132, only some of which are labeled, and cutting channel 134. In this figure, guide surface 116 on left guide sphere 112 is labeled. Also visible are an upper shell 104 and a lower shell 106 which together comprise outer shell 102. A channel 136 passes through outer shell 102 and allows movement of guide spheres 112 and 114. Channel 136 is explained in more detail below in conjunction with FIGS. 3 and 4.

Figure 3:
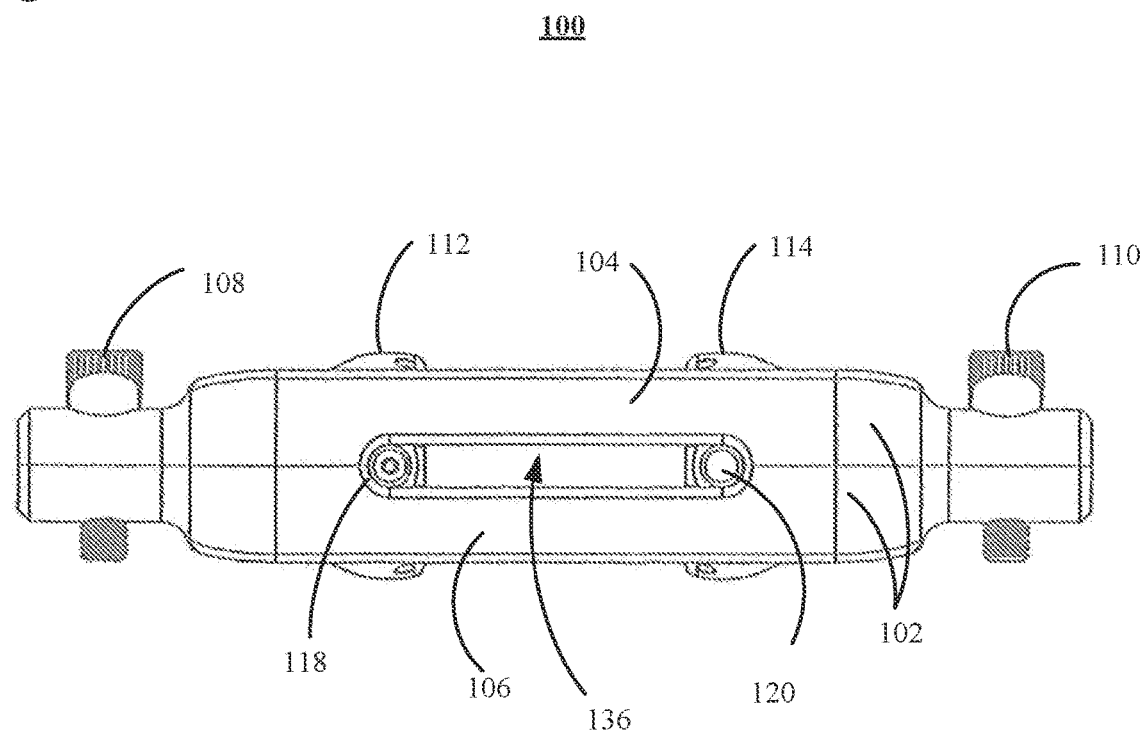
FIG. 3 is an illustration of the bone cutting guide of FIGS. 1-2 from a side view perspective.

FIG. 3 is an illustration of BCG 100 of FIGS. 1 and 2 from a side view perspective, visible in FIG. 3 are outer shell 102, which consists of upper shell 104 and lower shell 106, wing bolts 108 and 110, guide spheres 112 and 114, a guide post 118 that extends from left guide sphere 112 and through channel 136 (FIG. 2). A similar guide post 118 (see FIG. 4 extends from right guide sphere 114 on a side of BCG 100 that is obscured in FIG. 3.

Figure 4:
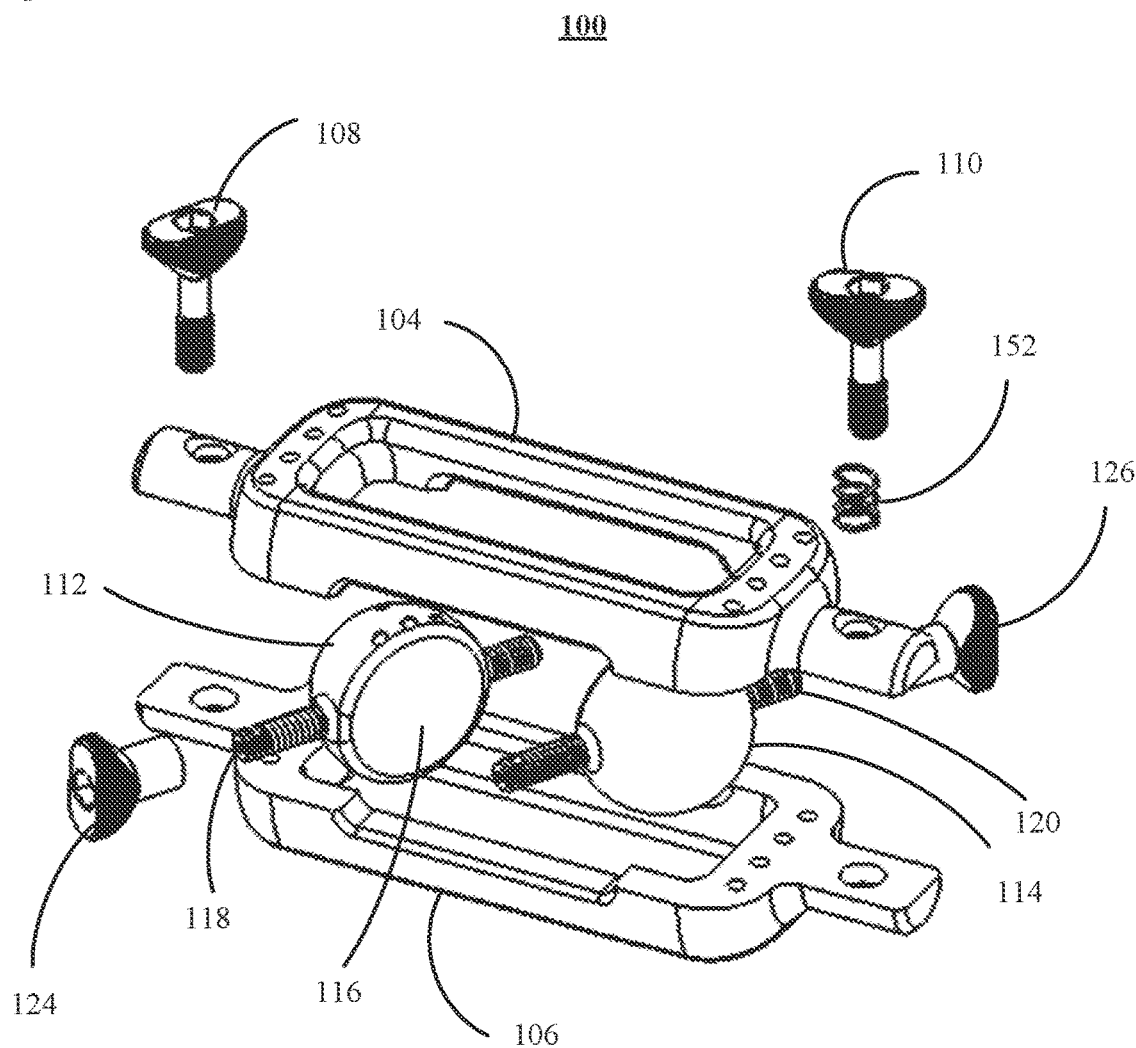
FIG. 4 is an illustration of the bone cutting guide of FIGS. 1-3 disassembled showing the component parts.

FIG. 4 is an illustration of BCG 100 of FIGS. 1-3 disassembled showing the component parts. Like in FIG. 1-3, upper shell 104, lower shell 106, wing bolts 108 and 110, guide spheres 112 and 114, guide posts 118 and 120, dome wing nuts 124 and 126 and cutting surface 116 on left guide sphere 112. In addition, FIG. 4 shows components that may not be visible in an assembled device. A spring 152 fits onto wing bolt 110. Although not shown, a spring may also fit onto wing bolt 108 to serve a similar purpose. Spring 152 and the one on wing bolt 108 push upper shell 104 and lower shell 106 lightly together prior to wing bolts 108 and 110 being tightened, thereby enabling left and right guide sphere 112 and 114 to be more easily positioned before left and right guide spheres 112 and 114 are secured in a desired position. In the alternative, spring 152 may be positioned on wing bolt 108 in between upper and lower shells 104 and 106 and be adapted to lightly pull upper and lower shells 104 and 106 together prior to wing bolts 108 and 110 being tightened.

Figure 5:
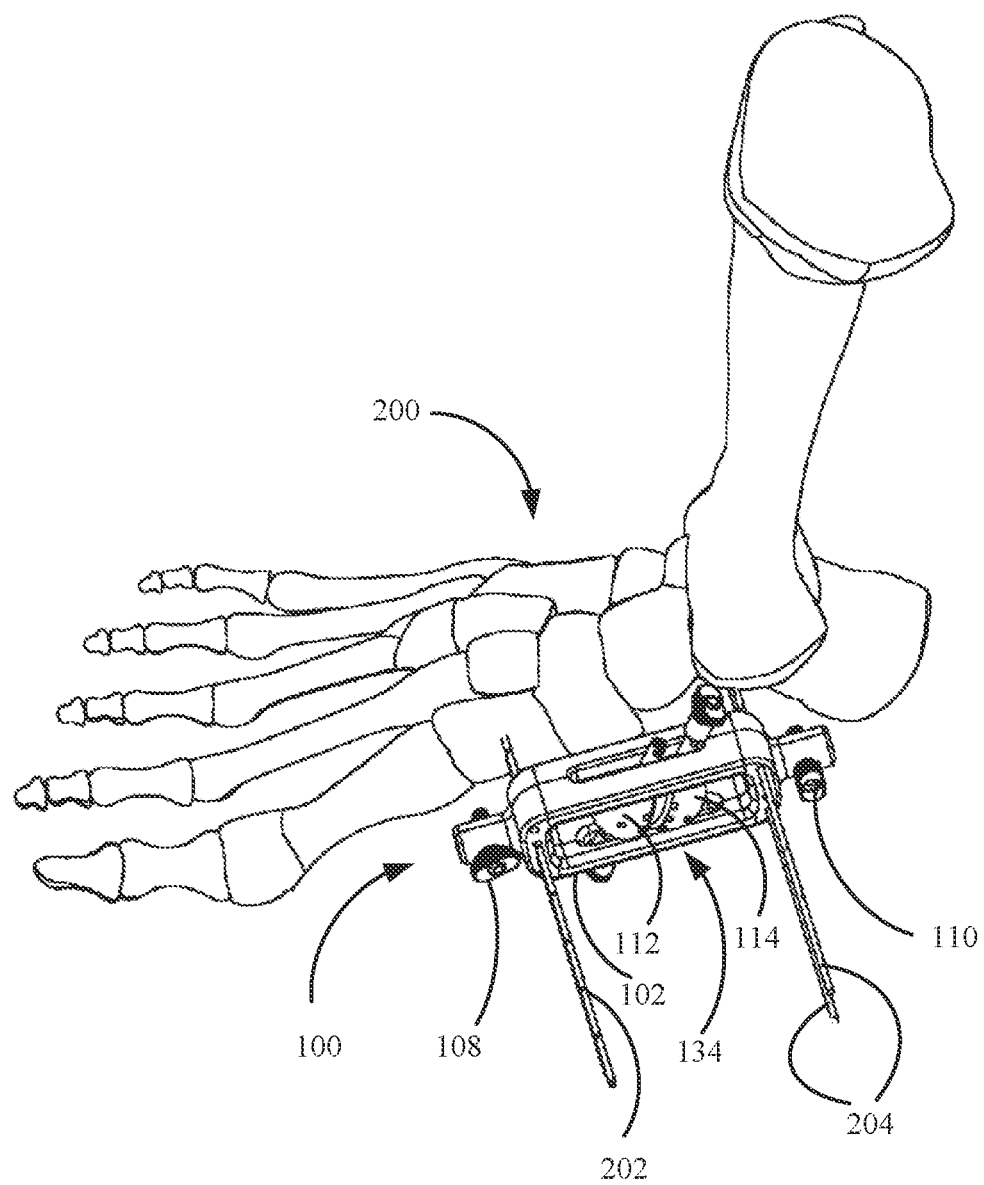
FIG. 5 is an illustration of the bone cutting guide of FIGS. 1-4 in position on a foot of a patient.

FIG. 5 is an illustration of BCG 100 of FIGS. 1-4 in position on the bones of a foot 200 of a patient. Like shown in FIGS. 1-4, FIG. 5 shows outer shell 102, wing bolts 108 and 110, guide spheres 112 and 114 and cutting channel 134 (FIGS. 1 and 2). In this example, a pin 202 has been inserted through a pin guide hole like pin guide holes 132 (FIG. 1) and then into foot 200. In a similar fashion, pins 204 have been inserted through a pin guide hole like pin guide holes 132 and then into foot 200. Pins 202 and 204 secure BCG 100 in a selected position with respect to foot 200.

When wing bolts 108 and 110 are tightened guide spheres 112 and 114 may be secured in a desired position. In this manner, guide surface 116 (FIG. 1) and the corresponding guide surface on right guide sphere 114 may be employed to enable a surgeon to make cuts with a surgical saw (not shown) or knife (not shown) through channel 134 to the bones of foot 200 at precise and desired angles, which enables the bones to then be fused back together at various selected angles.

In this example, the intention of this particular procedure is to make a precision bone Osteotomy that allows the reduction of a deformity. The current state of the art does provide a guided way to make such a cut. Rather, a surgeon blindly draws lines on an x-ray, looks at intraoperative imaging and then draws lines over the area to use as a guide. The claimed device orients the instrumentation to make the cuts in a precise manner. With K-wires used to stabilize the device, very precise cuts are facilitated, for example to correct a Charcot deformity or for joint fusion.

Figure 6:
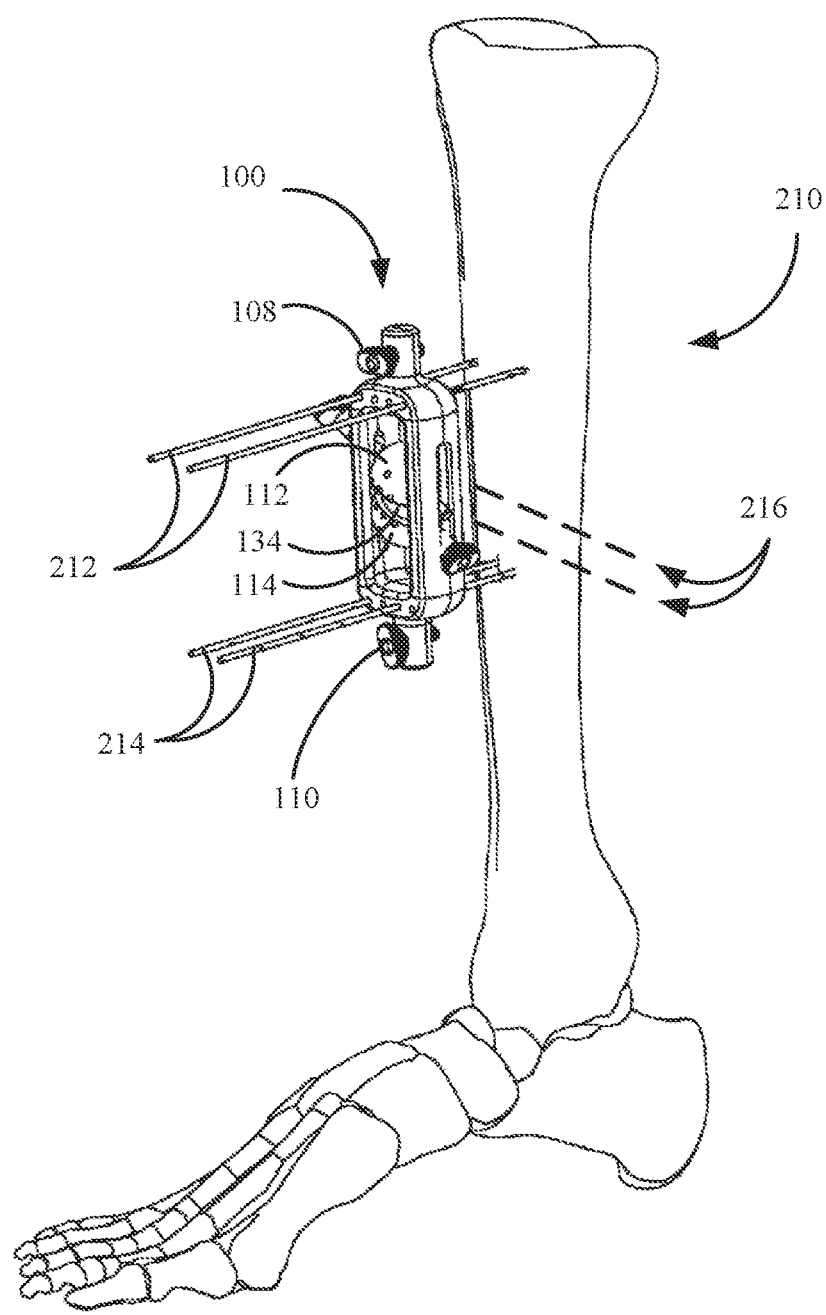
FIG. 6 is an illustration of the bone cutting guide of FIGS. 1-5 in position on a leg bone, or tibia, of a patient.

FIG. 6 is an illustration of BCG 100 of FIGS. 1-5 in position on a patient's tibia 210. Like shown in FIGS. 1-5, FIG. 6 shows wing bolts 108 and 110, guide spheres 112 and 114 and cutting channel 134. In this example, pins 212 have been inserted through pin guide holes like pin guide holes 132 (FIG. 1) and then into tibia 210. In a similar fashion, pins 214 have been inserted through pin guide holes like pin guide hole 132 and then into tibia 210. Pins 212 and 214 secure BCG 100 into a fixed position with respect to tibia 210. Two dotted lines 216 mark the position of cuts that would be made to tibia 210 when BCG 100 and its components are in the illustrated configuration.

Figure 7:
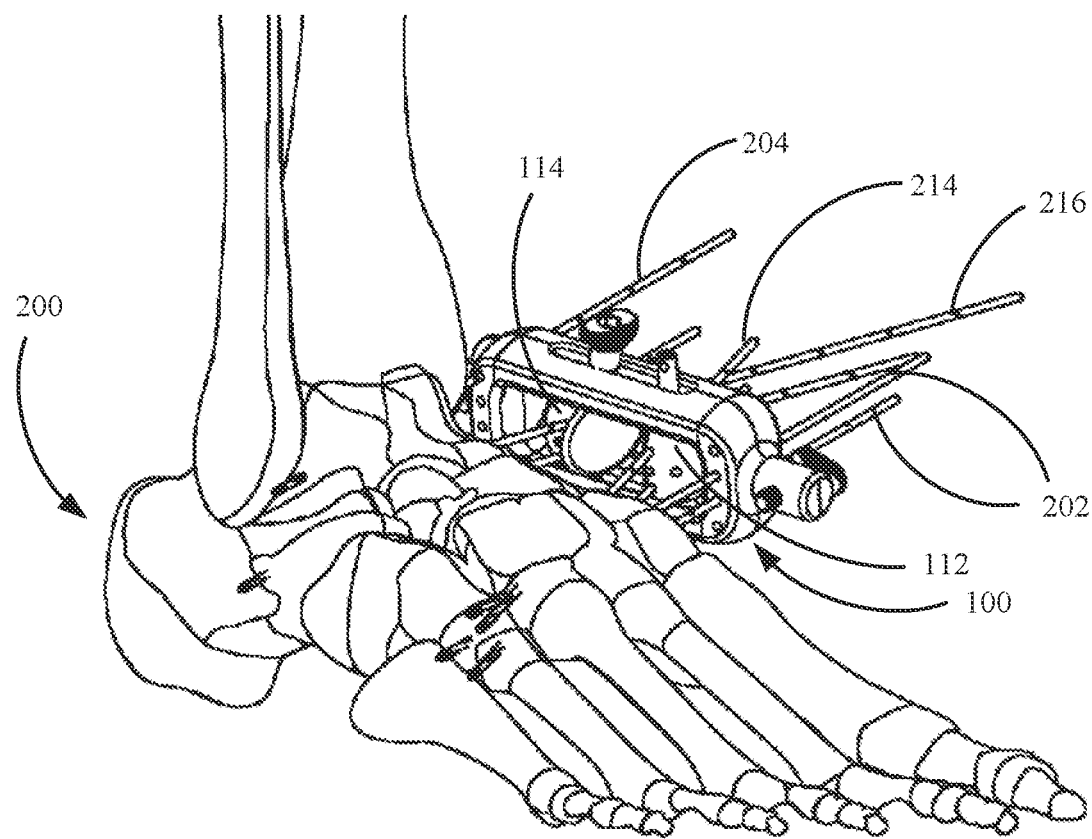
FIG. 7 is an illustration of the bone cutting guide of FIGS. 1-6 in position on a foot of a patient.

FIG. 7 is an illustration of the BCG 100 of FIGS. 1-6 positioned on foot 200 (FIG. 5). In addition to pins 202 and 204 that secure BCG 100 in a desired position with respect to foot 200, FIG. 7 illustrates the use of pins or wires 214, only one of which is labeled, to secure left guide sphere 112 in position. Also shown is the use of pins or wires 216, only one of which is labeled, to secure right guide sphere 114 in position. Although not clearly visible in FIG. 7, pins or wires 214 and 216 pass through wire guide holes like wire guide holes 130 (FIG. 1) in left and right spheres 112 and 114 and then into and, in this example, through foot 200. Pins or wires 214 and 216 may also be employed to guide a surgeon's cut, either visually or with the use of x-ray imaging.

While the claimed subject matter has been shown and described with reference to particular embodiments thereof, it will be understood by those skilled in the art that the foregoing and other changes in form and detail may be made therein without departing from the spirit and scope of the claimed subject matter, including but not limited to additional, less or modified elements.

We claim:

1. A device for facilitating the precision cutting of one or more of a patient's bones, comprising:
    an outer shell, comprising:
        an upper shell; and
        a lower shell;
    a plurality of pin guidance holes that pass through the upper and lower shells;
    a left guidance sphere, comprising a first guide surface;
    a right guidance sphere, comprising a second guide surface, wherein the left and right guidance spheres are positioned between the upper and lower shells; and
    a plurality of fasteners configured to hold the upper and lower shells together and, when tightened, secure the left guidance sphere and right guidance sphere into selected positions.

2. The device of claim 1, the left and right guidance spheres each comprising a plurality of wire guidance holes.

3. The device of claim 2, wherein the wire guidance holes are adapted to be threaded by one of a wire or pin and each pin or wire adapted to be secured into the patient's bone.

4. The device of claim 1, the left and right guidance spheres each comprising:
    a threaded guide post, and;
    a nut with a dome-shaped surface adapted to be threaded onto the threaded guide post such that the dome-shaped surface comes into contact with the outer shell and, when the nut is tightened, secures the respective guidance sphere with respect to the outer shell.

5. The device of claim 1, further comprising pins adapted to pass through the pin guidance holes in the upper and lower shells and each pin adapted to secure the outer shell in a fixed position with respect to one of the patient's bones.

6. The device of claim 1, further comprising a plurality of springs, each spring positioned on a respective one of the plurality of fasteners and adapted to push the upper and lower shells lightly together prior to the corresponding fastener being tightened, thereby enabling the guide spheres to be more easily positioned before being secured.

7. The device of claim 1, further comprising a plurality of springs, each spring positioned on a respective one of the plurality of fasteners and adapted to pull the upper and lower shells lightly together prior to the corresponding fastener being tightened, thereby enabling the guide spheres to be more easily positioned before being secured.

8. The device of claim 1, the plurality of fasteners comprising nuts.

9. The device of claim 1, the plurality of fasteners comprising bolts and nuts.

* * * * *